(12) United States Patent
Dodd

(10) Patent No.: US 7,807,344 B2
(45) Date of Patent: Oct. 5, 2010

(54) METHODS AND SYSTEMS FOR ENSURING THE SECURITY OF GRAIN STORES

(75) Inventor: Eric B. Dodd, Evansville, IN (US)

(73) Assignee: Global Grain Security, LLC, Owensboro, KY (US)

( * ) Notice: Subject to any disclaimer, the term of this patent is extended or adjusted under 35 U.S.C. 154(b) by 742 days.

(21) Appl. No.: 11/553,163

(22) Filed: Oct. 26, 2006

(65) Prior Publication Data
US 2008/0102485 A1 May 1, 2008

(51) Int. Cl.
*C12Q 1/00* (2006.01)
*G01N 33/02* (2006.01)

(52) U.S. Cl. .................. 435/4; 435/5; 435/6; 435/7.1; 435/7.32

(58) Field of Classification Search .............. None
See application file for complete search history.

(56) References Cited

U.S. PATENT DOCUMENTS

| | | | |
|---|---|---|---|
| 4,140,006 A | | 2/1979 | d'Auzac et al. |
| 4,502,951 A | | 3/1985 | Koenig et al. |
| 4,616,515 A | | 10/1986 | Dancoine |
| 4,930,359 A | | 6/1990 | Wolfrum et al. |
| 5,544,686 A | | 8/1996 | Kearney |
| 5,961,923 A | * | 10/1999 | Nova et al. .................. 506/4 |
| 6,406,725 B1 | | 6/2002 | Taylor |
| 6,406,728 B1 | | 6/2002 | Roth |
| 6,446,514 B1 | | 9/2002 | Danylewych-May et al. |
| 6,834,533 B2 | | 12/2004 | Megerle |
| 7,032,467 B2 | * | 4/2006 | Yoon ........................ 73/863.81 |
| 7,047,103 B2 | | 5/2006 | Hornbaker et al. |
| 7,060,225 B2 | | 6/2006 | Niehaus |
| 7,062,982 B2 | | 6/2006 | Coyle et al. |
| 7,073,748 B2 | | 7/2006 | Maurer et al. |
| 2007/0072255 A1 | * | 3/2007 | Kodukula et al. ............. 435/25 |

OTHER PUBLICATIONS

Nganje, William, Wilson, William, Nolan, James, "Terrorism and the Grain Handling System in Canada and the United States", Jul. 2003.
Seitz, L., Sauer, D., "Volatile Compounds and Odors in Grain Sorghum Infested With Common Storage Insects", Nonwheat Grains and Products, vol. 73, No. 6, 1996, pp. 744-750.
Sigman, M., Ilgner, R., Operational Guideline: Tenax Ta Collection and In-Injection Port Thermal Desorption Analysis of Trace Levels of Organic Explosive Vapors, Oak Ridge National Laboratory, Sep. 1, 2001.
Tetracore: Providing Advanced Solutions to Your Molecular and Immunological Needs, [online] Aug. 9, 2006; Retrieved from the Internet: http://www.tetracore.com/.

* cited by examiner

*Primary Examiner*—Eileen B O Hara
(74) *Attorney, Agent, or Firm*—Woodard, Emhardt, Moriarty McNett & Henry LLP

(57) ABSTRACT

Aspects include claims, systems, and methods for testing bulk grain stores to identify the presence of contaminants. Such contaminants tested for may include biological, chemical, or radio nuclear material. Another aspect is marking and/or tracking grain stores that have been certified as either being contaminated or safe. Still another aspect is an automated or automatic system for measuring the level of contamination in a given grain store, and for marking and tracking grain stores tested for contamination.

18 Claims, 6 Drawing Sheets

| SAMPLE No. | RFID TAG No. | DATE | TIME | LOCATION | TEST | VALUE |
|---|---|---|---|---|---|---|
| A-357 | D-312 | 9/12/03 | 11:32 A.M. | BTOWN | T-15 | >3.47 |
| A-346 | B-166 | 7/3/04 | 10:17 A.M. | CBURG | T-15 | >1.23 |
| A-371 | B-112 | 8/12/05 | 9:02 A.M. | BTOWN | T-15 | >2.64 |
| A-233 | B-018 | 6/1/05 | 7:23 A.M. | BTOWN | T-15 | >1.36 |
| A-310 | A-630 | 7/23/06 | 12:03 A.M. | BTOWN | T-15 | >4.28 |
| A-711 | D-312 | 3/12/04 | 7:51 A.M. | DVILLE | T-15 | >5.77 |
| A-441 | D-101 | 2/15/05 | 7:36 A.M. | BTOWN | T-15 | >1.11 |

*Fig. 5*

METHODS AND SYSTEMS FOR ENSURING THE SECURITY OF GRAIN STORES

FIELD OF THE INVENTION

Various aspects relate to testing grain stores for contamination and/or marking tested grain stores and tracking them from various points in the production of grain from harvesting to the retail market.

BACKGROUND

The production and marketing of grain and grain-related products world wide is a multi-billion dollar a year industry. In the United States along, about 2.1 million producers deliver about 300 million metric tons of grain to U.S.-based elevators each year and about 1.08 million railroad cars are used to transport grain; in all 23 million metric tons of grain are shipped by barge each year.

In the industrialized world, a vanishing small number of farm-related workers has generated a situation in which most people have very little actual contact with or knowledge of precisely where their food was grown, harvested, shipped, and processed. This also means that most people in industrialized nations live and consume foods far removed from where they are produced. This has led many officials and food safety experts to note how vulnerable the food production and distribution system is to either deliberate or inadvertent contamination.

Accordingly, there is a pressing need for methods to enable people to track potential contamination within the grain-based food chain. The need to insure a safe supply of food has always existed in the food industry. What has become glaringly apparent of late is that this chain is vulnerable to nefarious assault as well as natural and other man-made phenomenon.

The threat to the nation's food supply by "Agro-Terrorism" has been detailed in various reports, including, for example, "Terrorism and the Grain Handling System in Canada and the United States," by William Ngange, William Wilson, and James Nolan. The world-wide threat from Agro-Terrorism has been summarized in a report issued by the United Nations, World Health Organization in a report entitled, "Terrorist Threats to Food: Guidelines for Establishing and Strengthening Prevention and Response Systems." The World Heath Organization defines food terrorism as:

"The act or threat of deliberate contamination of food for human consumption with chemicals, biological and radio nuclear agents for pure reasons of causing injury or death to civilian population and/or disrupting social, economic or political stability."

These reports and the like focus on assessing the threat that contaminated foods, including, for example, contaminated grain stores, pose to civilian populations. These reports do not propose solutions, although both recommend increased vigilance of the food supply by those responsible for producing and transporting foods, including grain. Clearly, there is a threat to the world's food supply and there is a need for a means of testing, monitoring, and tracking foods including grains throughout the food producing system.

Still another concerning for many consumers both in the Untied Sates and abroad is the unintended commingling of food groups with a genetically modified organism (GMO). Many consumers expressed a clear preference for varieties of grains that are free of GMOs. Many GMO plants are almost identical to non-GMO plants, differences in some instances being only one or a handful of genes. This makes differentiating between grains that are derived from a GMO plant versus non-GMO plant derived claims very difficult. One approach is to carefully document the source of all of the grains and to certify the origin of the food-stuff in one practice within the industry such food-stuffs are referred to as 'identity? preserved'. The current approach does not provide a ready method for widespread easy testing of bulk grain stores to empirically certify that the grain is GMO free.

Various aspects disclosed herein address the need for efficient means to test for and determine the presence of various contaminants, including chemical and microbiological agents as well as GMOs in bulk grain stores.

SUMMARY

One embodiment is a method for checking the safety of edible grains, comprising the steps of providing a bulk quantity of edible grain in a container, after harvesting the grain and before processing the grain into a final food product; passing at least a sample of gas-borne material once in contact with a grain store through a capturing media; extracting at least some of the particulate matter from the capturing media; and testing the matter for the presence of various contaminants. One embodiment includes testing grain for contaminants selected from the group comprising: anthrax, *brucella*, ricen, botulinum, plague, tularemia, staphylococcal aureaus, *e-coli*, various toxic fungi, and molds and contaminants such as heavy metals including mercury and lead, various levels of pesticides and herbicides, radioactive material, and genetically-modified plant matter.

In some embodiments capture media includes a device for recording the time and location at which a given sample was collected, in one embodiment the device is in the form of an RFID tag and it may incorporate global position capability to record the location of the capture media when it was used or the device collected for further analysis. In some aspects the device may be used to transfer data concerning the location of the capture media at the time of sampling to a data base. The data base may also include data concerning subsequent analysis of the sample and these data streams may be mated to provide a history of the sample from capture to analysis. The data may also be used to provide information on the particular grain store from which the sample was originally captured.

One embodiment includes a pulsed sampling technique to help ensure that the sample collected in the capture device is representative of the gas in contact with the grain store being sampled.

Stages in grain processing and transport in which the grain is being moved in part or in bulk present attractive opportunities for gather statistically significant samples of materials that were in the grain and were associated with gases that are or were in contact with the grain.

In one embodiment, the capture media may include at least one of the following: a filter, a static dust collector, a scrubber, a bubble tube, or any combination thereof.

In one embodiment, after a particular grain store has been checked for contamination, the checked batch is marked to identify the contamination status of the batch.

In another embodiment, the checked batch is marked by inserting a Radio-Frequency ID (RFID) device into the grain. In still another embodiment, the store is marked by means of coating, spraying, and/or dyeing the grain a particular visible color, or ultra-violet hue, preferably using an edible material.

In one embodiment, a sample of material collected from the capture media is examined using any of a variety of analytical techniques, including, for example, a Geiger counter, to detect the progress of a radioactive contaminant or any of the following other analytical techniques including, for example, absorbance measurements, fluorescence measurements, antibody binding determinations, polymerase chain reaction, or various arrays which may include on a surface or a series of surfaces a number of different materials that specifically interact with various contaminants. Materials that interact with contaminates may include, for example, antibodies, each sensitive to a specific antigen or oligonucleotides that selectively hybridize to specific components of various contaminants.

In one embodiment, a sample collected from a capture media is marked with a unique code, and this code is used to track that particular sample, and by inference the bulk grain store from which that sample was collected, throughout the rest of the food monitoring process.

In one embodiment, the grain store is monitored within a given grain processing facility. In still another embodiment, the grain store may be monitored from place to place up through, and including, actual delivery to a processing plant in which a particular grain store is converted into a food-stuff.

In one embodiment, an automated system is used to alert either human or computerized monitors to the fact that a batch of grain has tested positive for contamination. In one embodiment, contaminated stores are flagged and tracked, for either removal from the system or decontamination. In still another embodiment, information that a store of grain is contaminated generates an alert that may be any form including a siren, strobe, e-mail, telephone call, facsimile transfer, or any other means of drawing attention to the fact that a particular sample has tested positive for a given contaminant.

Various sampling devices are envisioned within various embodiments, these supply devices include sampling a given volume of gas in contact with a grain store, in order to create a sample that is representative of the content of a particular grain store. In one embodiment, the samples are collected at an interval ranging from between ten minutes to six hours or more. In some embodiments, the length of time over which particular samples are collected and tested can vary according to the needs of a particular operation and the capacity of the sampling system.

BRIEF DESCRIPTION OF THE DRAWINGS

FIG. 5 is a hypothetical representation of the typical report which could be generated according to various embodiments.

DETAILED DESCRIPTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

DEFINITIONS

Terms used herein are given their usual and customary definitions unless stated otherwise.

GRAIN STORE: Any facility or structure used to store harvested grain in bulk. (Example: a grain bin, flat storage, storage tank, a barge, a railroad car, or a truck used for the transportation of grain.) A grain store may be on farm storage, a commercial elevator or bulk grain held by an end user. The term may also refer to the bulk storage tank on a grain harvester "combine".

GRAIN ELEVATOR: A common term used for a commercial facility that stores bulk grain. The term is sometimes used to describe a piece of equipment used to elevate grain (see ELEVATOR).

ELEVATOR: A piece of equipment used to elevate grain from ground level into a grain storage structure. Common terms for an elevator may include an elevator leg, leg, or grain elevator.

FLAT STORAGE: A common term used for describing the storage of grain on a flat surface such as a building floor or the ground.

STORAGE TANK: A structure used for storing grain, such as a grain bin, a bulk tank, etc.

CONVEYOR: A piece of equipment generally consisting of a chain or belt that is used to transfer grain to or from storage.

AUGER: A piece of equipment that generally consists of a round tube containing a screw or flight that is used to transfer grain to or from storage.

COMBINE: A piece of equipment used to harvest grain. Generally self propelled and containing a bulk storage bin for grain.

GRAIN DRYER: A bulk storage bin built using perforated sides so that heated air may pass through the grain to reduce the moisture content.

BATCH: One grain store unit. (Example: barge, railcar, truck, ship hold, or grain silo.)

COMPOSITE: Uniform mixture of strategically collected grab samples.

GRAB SAMPLE: A sample collected from a specific location within a specified time of a specific amount (all determined on statistical requirement).

Figure 1:
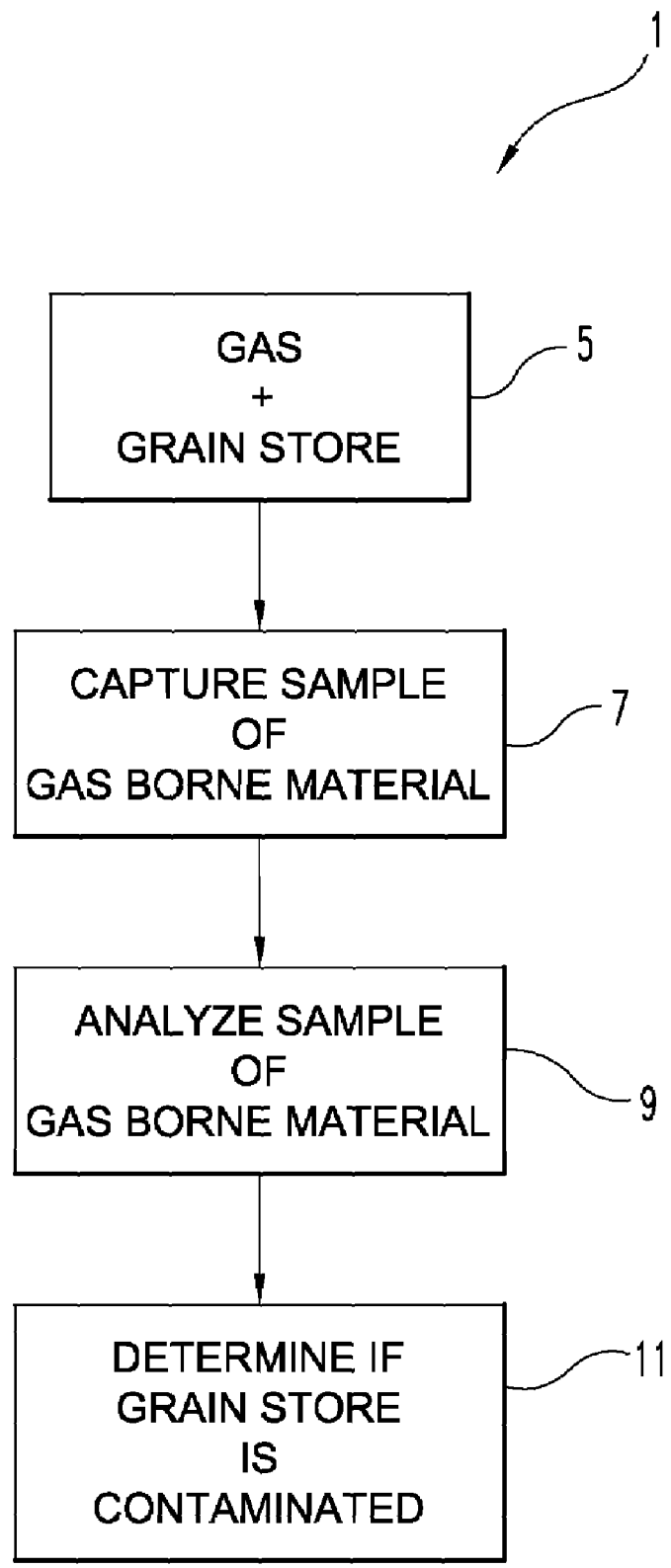
FIG. 1 is a block diagram illustrating various steps in one embodiment.

There is a great need for an economical and effective means of testing grain at various stages of its harvest, transport, and processing to determine and verify that a given shipment of grain is contaminant free when it is delivered to a food processing plant. Various embodiments are directed towards meeting this need. Referring now to FIG. 1, block diagram 1 illustrates various steps in one embodiment. These steps include, but are not limited to, providing a grain store which includes a gas 5, generally air. In one aspect, the gas is located in the headspace of a device or structure used for storing grain in bulk, for example, a grain elevator, storage tank, railroad car, closed truck, shiphold, or the like. Another step illustrated in FIG. 1 is sampling gas that includes gas-borne materials; for example, material including particulates associated with the grain are captured on capture media 7. Next, the gas-borne material collected from the captured media 2 is analyzed 9. In still another step of this embodiment, a determination is made as to whether or not a particular grain store is contaminated 11.

Figure 2:
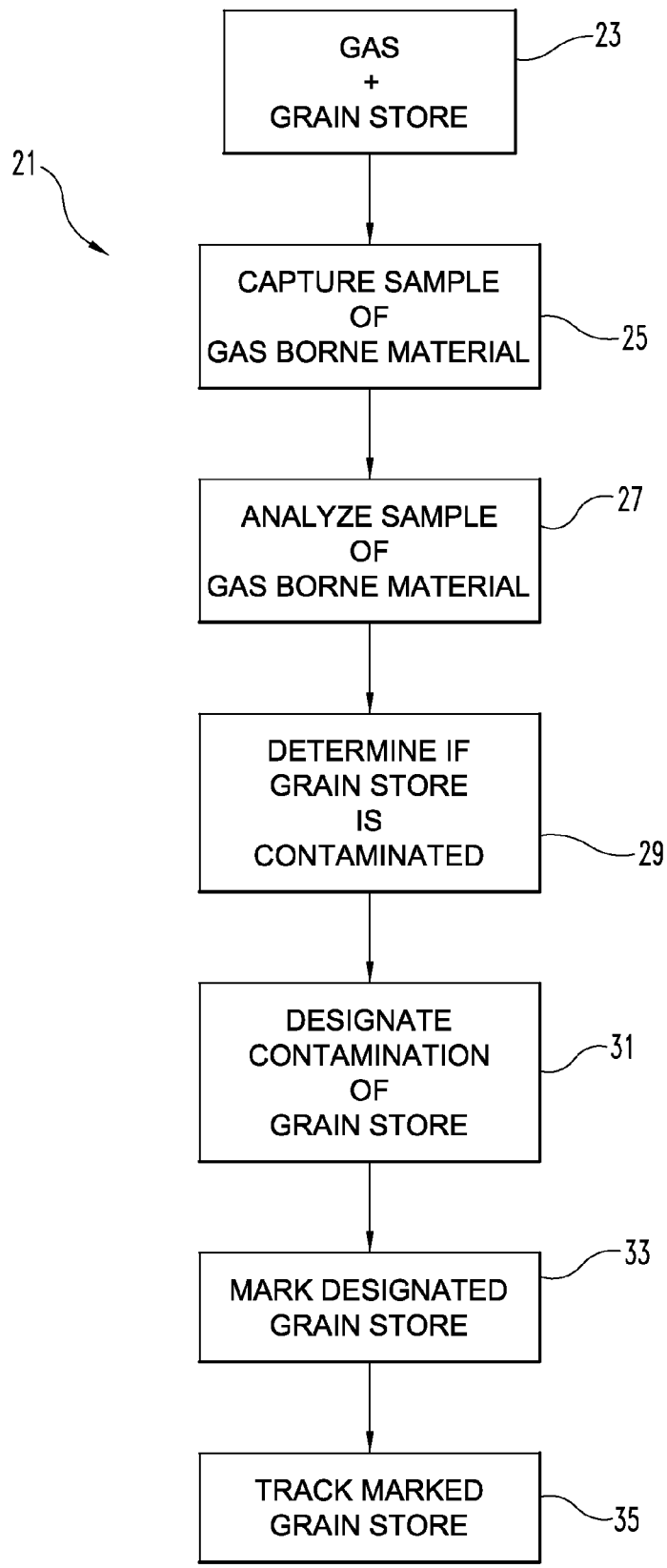
FIG. 2 is still another block diagram illustrating various steps in one embodiment.

Referring now to FIG. 2, block diagram 21 illustrates various steps in some embodiments. Steps included in these embodiments comprise providing a grain store having a gas associated with it that is or was in contact with at least a portion of the grain store 23. Another step includes capturing a sample of the gas-borne material 25, preferably a sample from a statistically significant sample of gas. Another step of this embodiment is analyzing the sample of gas-borne material collected 27 from the gas sample. Next, the results of the analysis performed in step 27 are used to determine if the grain store is contaminated 29. Based on the determination made in step 29, a grain store may be designated as either safe or contaminated 31. Next the grain store is marked as being safe or contaminated 33. A further step illustrated in these embodiments involves tracking the marked grain store 35 in order to ensure that the material is safe once it arrives at the next destination in the grain transport system.

Figure 3:
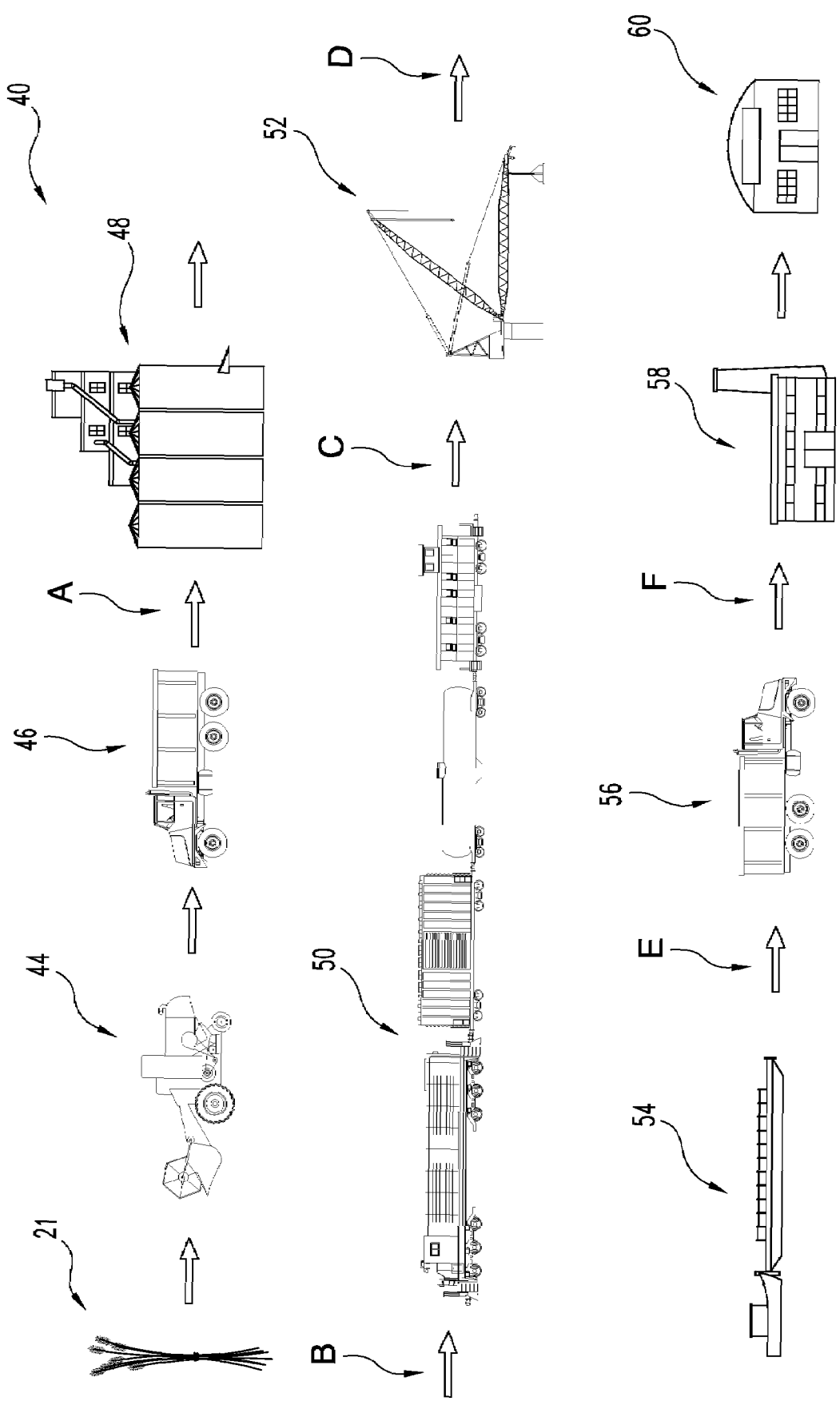
FIG. 3 is a schematic representation of various steps in the process of growing and bringing to the retail market grain and grain-related products.

Referring now to FIG. 3, illustrated herein are various steps commonly found in the process of growing, harvesting, and transporting grain to the retail market 40. Various steps include harvesting, for example, wheat 21 using a mechanized device 44, for example, a combine. Next, harvested grain is loaded onto a truck 46 for delivery to a grain storage facility, for example, a grain elevator 48. Next, material grain stores accumulated in the elevator are loaded onto a train including, for example, railroad cars suitable for the containment of grains 50. Next, the grain may be delivered to a dock for eventual loading 52 onto a barge or ship or other type of container vessel 54. After transport via ship or barge, a grain may be offloaded onto another form of transportation, for example, a truck 56 which is used to deliver the grain to a food processing plant 58. Ultimately, the grain is incorporated into a food-stuff, for example, bread, for delivery to a retail market 60. Various places that can be sampled to check for contamination include batch stores, storage tanks, elevators and the like.

In still another embodiment a sample is collected from a bulk gain store such as the hold of ship and placed into a drum or other confined space. The grain in the drum may be aerated or mixed to produce a gas, for example, air that has been in contact with the grain and now carries a portion of the material that is the grain or is mixed in with the grain in the drum. This technique may be useful for sampling settled grain stores in that grab samples can be taken from various positions within the store that are not in contact with bases in the headspace of the grain container. It is an especially useful approach when gases in the headspace of grain storage are not expected to include solid material that is representative of the material in the bulk grain store. In one embodiment rather than testing each grab sample individually multiple grab samples may be combined to form a composite sample and the composite may be tested for the presence of contaminants including GMOs.

Further as illustrated in FIG. 3 there are various points in the grain harvesting and transportation chain where it may be particularly advantageous to sample the grain. Early on in the process, for example, at step A, it may be useful to sample each load of grain from individual trucks to ensure that the grain in each truck is safe before it is mixed in with the bulk material in the grain elevator 48. Catching a contaminant at this level could be particularly useful in that it would prevent a large amount of grain from becoming contaminated. Another point at which the grain supply can be checked for contaminants is B when the grain from the grain elevator is off-loaded to another medium for further delivery, such as by railroad car. Yet another place where the grain can be sampled is when it is delivered to or from a loading dock C. Sampling at this stage is important as the grain is being agglomerated, and inadvertently mixing in a portion of contaminated grain may contaminate a large store of grain. The contents of perhaps an entire train load of train cars collected from a number of different grain elevator stores for delivery to, for example, a ship or a barge may be sampled and tested. Material on the ship or barge may ultimately be offloaded at yet another dock and still another port, presenting still another sampling opportunity E. Just before delivery F of the grain to its processing plant is still another opportunity to sample the grain. Sampling at F may be a particularly important step in that grain at this stage is destined for immediate use as a food product for human or animal consumption. Accordingly, this is a particularly valuable place in the transfer chain to test the grain and ensure that the grain is safe for human consumption. Ultimately, assuming that the grain has been adequately tested through collection and delivery steps 21 through 56, the burden for ensuring the safety of the food-stuff now shifts to the food processing plant 58.

Other steps in the grain handling process where representative samples can be gathered include sampling gases, especially air, in and around conveyors, augurs, combines, grain dryers and the like.

Various aspects provide novel and useful ways for sampling and testing the grain as well as for marking and tracking, and thereby ensuring the safety of the grain at various steps along the pathway of producing the grain and ultimately converting it into a food-stuff.

Figure 4:
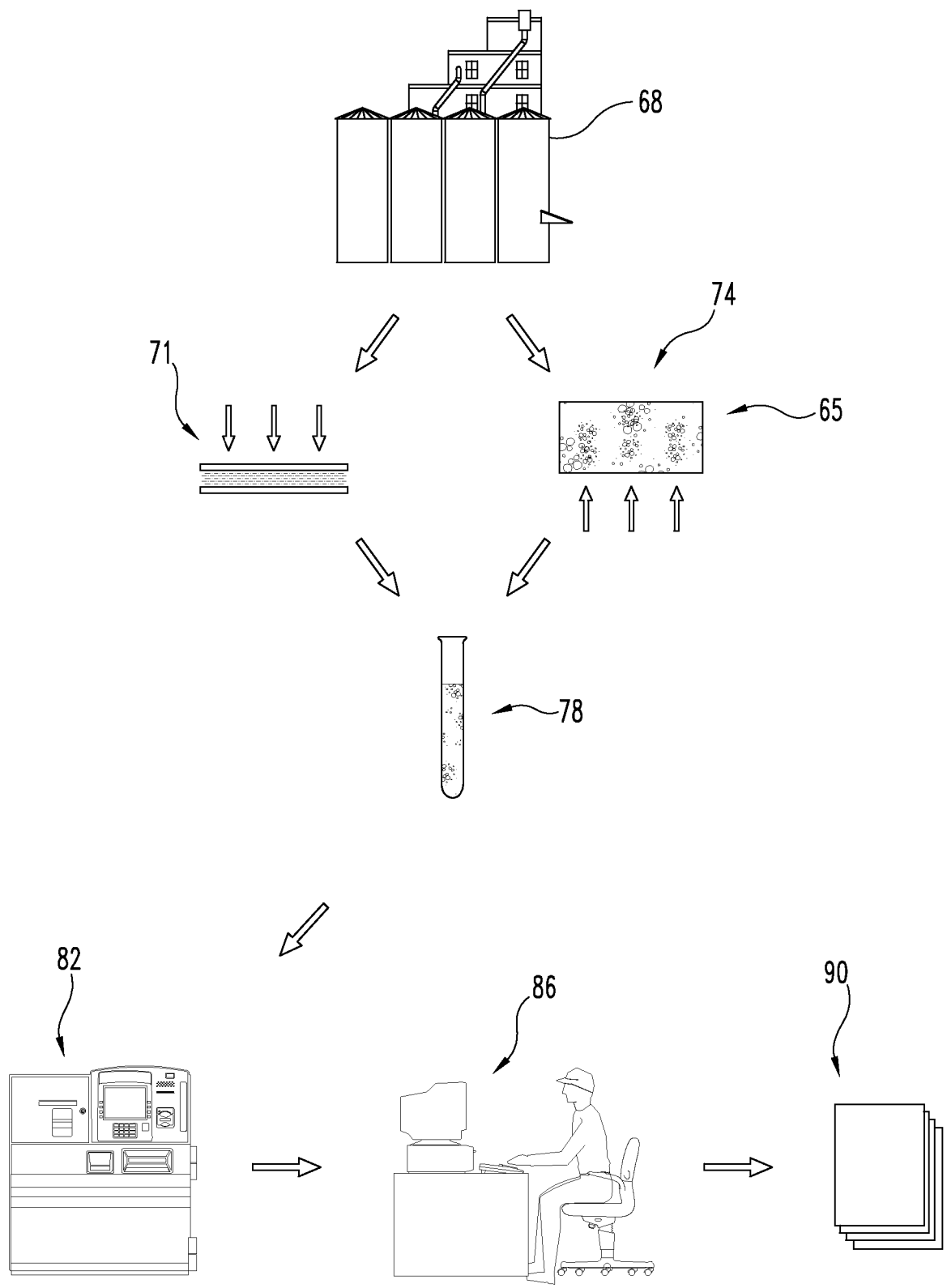
FIG. 4 is a schematic representation of an embodiment involving sampling a grain store, preparing the sample for analysis, analyzing the sample, and generating a report including data gathered on the sample.

Referring now to FIG. 4, illustrated herein is a schematic diagram 65 of various ways in which a particular grain store, for example, grain in a grain elevator 68, may be sampled and analyzed to determine if it is contaminated. As shown herein, a capture media in the form of a filter 71 or an electrostatic filter 64 or, not illustrated but just as easily implemented, a sparger may be used to collect a sample of matter associated with gases that are in contact with the grain store. Samples from any of these capture media may be prepared and placed into a suitable form 78 for analysis using some type of chemical, physical, electrochemical, electro physical, or biological assay. In FIG. 4, equipment for assaying samples is illustrated as a piece of equipment 82. The next step in the process of testing the grain for contaminates is to produce test data perhaps in the form of a numeric output fed to a computer shown as 86 which ultimately generates a report 90. The results of these analyses and the subsequent review of the report can be used to make decisions as to whether the grain is, or is not, contaminated and whether it should be marked as uncontaminated or contaminated. In one aspect, grain tested for contamination is also marked at this stage for tracking throughout the rest of the grain processing steps as illustrated previously in FIGS. 1 and 2.

Referring now to FIG. 5, illustrating a typical report 91 as may be generated by testing and tabulating data collected from testing grain stores. Typically data in report 91 may include, for example, sample number 93, an RFID 95 tag number, which may indicate information about which capture media was used, when and where the sample was drawn, and the like. Additional information in table 92 may include the date 97 and time 99 on which the sample was collected and the location 101 where the sample was collected. Location data 101 can include, for example, information such as the following: the name of the city, town, plant, storage bin, railroad car, truck, barge, ship, elevator, and the like. Table 91 may also include a column designating the type of test performed on a given sample 105 and the value measured 103 using a given test 105.

Figure 6:
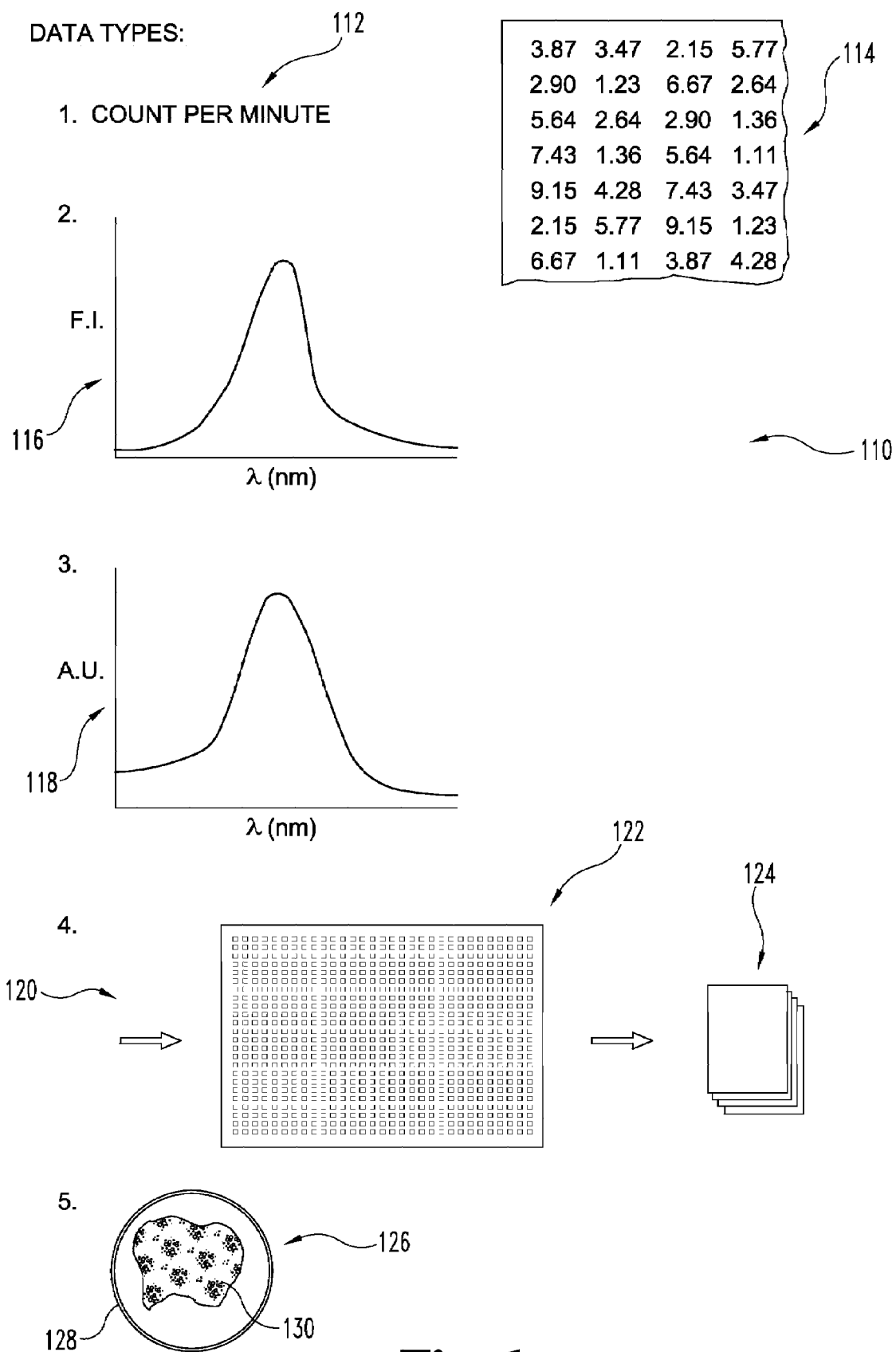
FIG. 6 is a schematic representation of various types of data related to the content of a grain store that can be collected in conjunction with various embodiments.

Referring now to FIG. 6, illustrated here 114 are various analytical tools that can be used to test particulates from gas associated with a grain store to determine if the grain store is contaminated. These tests include, but are not limited to, for example, counts per minute (1) which is commonly used in order to determine whether or not a radioactive contaminant is present in a particular grain store. Tests for radioactive contaminants often produce numerical values which are best presented in tabular form 114. Tests for radioactive materials may be accomplished by use of a Geiger counter, scintillation counter, or similar equipment.

Similarly, particulate samples may be tested directly or processed and then tested to determine if there is a florescent compound or signal 116 which is indicative the presence of a contaminant in the sample. Similarly, uv-absorbance 118 may be used to measure contamination levels in a given sample. Alternatively, material in a sample may be tested for contamination using an array 120; as shown herein 122 may be an array or stack of arrays 124. Arrays can include anything from nucleotide fragments which are known to hybridize complimentary nucleic acid sequences, to reagents that react with certain chemical contaminants. In one embodiment the array is comprised of a series of antibodies which selectively bind to specific antigens which are known to be, or thought to, associated with various contaminants.

One embodiment includes using the Elisa Kit developed by Tetracore, GGS to provide results on biological samples within a few hours. Some tests for chemical contamination generate results available in a day or less on all incoming shipments of grain. In one embodiment, any positive results are laboratory confirmed by follow-up testing within 72 hours.

Still another type of testing illustrated in 126 includes plating a sample of the particulate material recovered from gas in contact with the grain store on a plate 128. Some embodiments include using growth medium that selects for the growth of specific types of pathogenic microorganisms 130 which may be contaminating the grain. Evidence of growth in a specific set of plate conditions can be correlated with the presence of a contaminant of biological nature in a given grain store.

Ultimately, any one of these various analytical steps and many not shown can be used to generate a report which will enable the operator to make a determination as to whether or not a particular grain store is contaminated.

Additional testing for biological contaminant can be performed by blacklight and chromatography if cross qualitative analysis is required.

One embodiment includes forming a composite sample. The composite is a batch consisting of, for example, five to ten pounds of grain per total composite. The samples can be collected remotely by an intrusive device designed to penetrate a grain store to a desired location, then opened and used to remove a sample from the desired location. The samples can be visually examined and stored in a collection device ('40' gallon poly drum) for head space air collection and specific analysis as described in the above section. The amount of material collected in this manner may increase the statistical confidence in the sample by producing a sample that is representative of the bulk grain store. The sample may be aerated to increase the amount of particulate material in the head space associated with the sample. This approach can be used to produce a profile of grain stored in a bulk storage environment, eliminating the potential for statistical deviation created by drawing a single sample from a large grain store. As such, 90 to 99 percent confidence testing can be achieved through collecting a statistically appropriate amount of grain from the appropriate amount of locations based on the grain store.

One aspect includes visually marking an agricultural commodity before or after a processing step. In one embodiment, the markers are colored plant protein-derived pellets that can be made in different sizes and shapes for mixing into various agricultural commodities as a visual label or "taggant" during storage and shipment. The embodiments may greatly simplify the tracking and identification of commodity products in storage or in transit.

One embodiment includes a method and/or system for tracking transported grain. A radio-frequency identification (RFID) tag is provided for deposit in a container along with the grain. In one embodiment, the tag is dimensioned to approximate a size of an individual grain, and comprises a memory and RF communication channel. See, for example, U.S. Pat. No. 7,047,103. The RFID tag may further comprise data stored in the memory, the data including, for example, a time when the RFID tag was handled along with surrounding grain, information sufficient to determine a location of handling at the time the RFID tag was handled with the surrounding grain, and the purity of the grain store.

One embodiment includes a physical marker tracing caplet that possesses physical and chemical properties similar to native grain or other bulk products, does not segregate during handling, and can contain bar coding that identifies grain and other products from an individual field or location. One embodiment utilizes scanning technology and a data retrieval and management system that can trace grain and product movement and is scalable to handle the entire U.S. grain marketing system. The confidential database will also provide information on any agri-chemicals applied during production, handling or storage.

Various embodiments may include methods of identifying the source of grain (field level) at any point in the marketing system. The methods include marking the grain store by, for example, the addition of tracking beads that are readily removed from 2 kg grain sample using laboratory grain cleaning equipment to identify grain origins in a bulk shipment, have printed codes that identify the specific field of origin, contain a translucent coat to protect the printed codes during handling, and are added to the grain on a scale sensitive amount to provide statistical confidence that grain from an individual field is contained or not contained within a bulk of shipment of grain. Another embodiment includes adding colored plant protein-derived pellets to designated tested stores of grain. See, for example, U.S. Pat. No. 6,406,728 B1.

Example 1

Particulate samples will be collected for analysis using a dust collection system at two points, which will be chosen based on the design of the grain processing facility. These samples will be collected using air pumps connected to particulate filters. The pumps will be calibrated such that the equivalent amount of air from the elevator is pushed through the particulate collector for each sampling event. The particulate filter will be changed out each hour of operation for sampling for contaminants of concern.

The filter will be changed hourly for sampling. The filter will be placed into a separate container for transport to an area set aside for field sampling. A background sample will be collected by running the particulate filter in the elevator when it is not running and/or by taking particulate samples for the outside air in the vicinity of the grain elevator. These background samples will be analyzed in the same fashion as the samples collected in the elevator.

Example 2

Field screening of the particulate matter collected on the filter for biological contaminants uses the Tetracore Bioalert immunoassay test strips. Each of the field test protocols used for sample collection and preparation are identical. A Guardian Reader will be used for analyzing these test strips which provides assurance screening results are not misread in the field environment.

At the beginning of each day, samples will be collected and a proficiency test will be conducted using the Proficiency Test Strips from Tetracore to insure that the system is working properly. Proficiency Test Strips have both a positive and negative response so that the Guardian Reader can be checked to insure that it is in proper working order.

Sample preparation procedures for the Tetracore Bioalert immunoassay test strips are the same for each of the biological agents being assayed. The sample vial is first filled with 1.0 mL of sample buffer solution. An applicator swab is moistened with the sample buffer solution then used to collect the solid particulates from the filter, only one microgram per milliliter is required to run these tests. The applicator swab is placed into the sample vial with 1.0 mL of sample buffer solution. The applicator swab may be rotated for 10 seconds in the sample buffer solution. The applicator swab is pressed onto the inside of the sample vial to squeeze out any excess sample buffer solution before properly disposing of the swab. Next, the cap on the sample vial is closed, and sample is agitated for 10 seconds. The sample vial is then allowed to sit for 10 to 15 seconds allowing large particles to settle to the bottom of the vial. The sample is tested to insure that the pH is between 4 and 10; if the sample is not within this range, it will need to be diluted 1:4 before continuing with the analysis. Using a disposable bulb dropper, liquid is collected from the sample vial below any foam level but above any solid particles that have settled. Next, the immunoassay test strips are dosed with 5 drops of liquid then placed into the Guardian Reader.

The Guardian Reader upon Startup performs an Automatic internal calibration prompting the user for Sample ID information and choice of Reading Mode (Manual or Automatic). After applying the sample to the test strip, the Bioalert test strip is inserted into the Guardian Reader. The Guardian Reader begins operating after the User presses “Start”. The Reader automatically scans the Radio-Frequency ID (RFID) chip embedded in the Bioalert test strip and verifies the test type and calibration data for the particular type of test and lot number. After 2 to 3 minutes (in Manual Mode; Automatic Mode read time is approximately 15 minutes), the Reader automatically reports results on the LCD Display and Prints a report to the Personal Printer. Data displayed includes: Test Type, Result (Positive or Negative), Date/Time, Sample ID. Results are simultaneously saved into internal memory for recall later or for downloading to a computer for backup. Each Bioalert test strip is individually serialized for chain-of-custody and forensic documentation.

Do not dose test strips until the Guardian Reader is available for use, as the test strips are not usable 25 minutes after application of the sample. Time for each sample preparation and analysis is closely observed.

If a sample tests positive for any biological or chemical contaminants, the test will be re-analyzed completely with a new sample created as stated above and a new test strip. Toxin tests are extremely sensitive; it may be necessary to perform a 1:40 dilution of the sample to insure that there was no over sampling. If the sample still comes back positive it will be placed in a biological shipment container for delivery to an accredited outside lab for confirmatory analysis. Once a sample that tested positive for a contaminate is properly contained for shipment, the testing area will be properly decontaminated to insure no crossover contamination of future samples.

Example 3

Samples for metal analysis will be prepared using a microwave digestion protocol (Method 3051 SW846). This method will allow the preparation of multiple samples at one time along with quality control samples to insure proper handling. This procedure will require 0.5 grams of particles from the filter to be digested using nitric acid (HNO3). The solution will then be brought up to a total volume of 100 mL for ICP analysis. A lab blank and matrix spike will be included in this sample preparation.

Before analyzing the samples the ICP will need to be calibrated with a method blank, instrument blank, ICV (initial calibration verification), and CCV (continuing concentration verification). Once the system is calibrated the samples will be analyzed, by using an ICP or ICP-MS instrument for this analysis it will allow for multiple metal analysis for each sample. Methods 60 1Ob or 6020 USEPA SW 846 will be used for these analyses.

Example 4

The purpose of this test will be to screen for the 10 most predominant organic constituents in the filter collected sample. This will be conducted by extracting the samples collected on the filter for both water and non-water soluble organics then analyzing these samples on a GC-MS.

Method SW-846 3545 will be used to extract the filter collected sample. This method will utilize an Accelerated Solvent Extraction (ASE) instrument. Samples will be collected using solvents specifically for creating water and non-water soluble samples for analysis (Acetone, Methylene Chloride, Hexane . . . ) that are suitable for this analysis. Concentration of the sample maybe conducted to increase the sensitivity of the instrumental analysis on an as need bases.

A GC-MS will be used to analyze the extracted samples; the GCMS will be set-up for each analysis based on manufacturer’s protocols for the analysis of water and non-water soluble organic analysis. The ten highest peaks, more if required for specific contract requirements, will be quantified for chemical constituents.

All references, patents, patent applications and the like cited herein and not otherwise specifically incorporated by references in their entirety, are hereby incorporated by references in their entirety as if each were separately incorporated by reference in their entirety.

An abstract is included to aid in searching the contents of the application it is not intended to be read as explaining, summarizing or otherwise characterizing or limiting the invention in any way.

The present invention contemplates modifications as would occur to those skilled in the art. It is also contemplated that processes embodied in the present invention can be altered, duplicated, combined, or added to other processes as would occur to those skilled in the art without departing from the spirit of the present invention.

Further, any theory of operation, proof, or finding stated herein is meant to further enhance understanding of the present invention and is not intended to make the scope of the present invention dependent upon such theory, proof, or finding.

While the invention has been illustrated and described in detail in the figures, formulas and foregoing description, the same is considered to be illustrative and not restrictive in character, it is understood that only the preferred embodiments have been shown and described and that all changes and modifications that come within the spirit of the invention are desired to be protected.

What is claimed:

1. A method for checking the safety of a particulate food store, comprising the acts of:
   (a) providing a bulk quantity of particulate food;
   (b) passing gas that was in contact with the bulk particulate food through a capturing media leaving material to be tested in said capturing media, wherein the gas is a composite sample representative of the bulk food store; and,
   (c) assay testing said material from the capturing media for the presence of contaminants.

2. The method of claim 1, wherein said material is analyzed for the presence of at least one contaminant selected from the list consisting of: anthrax, *brucella*, ricen, botulinum, plague, tularemia, staphylococcal aureaus, pesticides, herbicides, genetically-altered plant matter, and radio nuclear materials.

3. The method of claim 1, wherein said capturing media is marked with an identifier to identify at least the date and sample location captured by the media.

4. The method of claim 3, wherein said identifier includes a radio-frequency identification marker or bar code that is unique per capturing media.

5. The method of claim 3, further including a computer memory data storage system, and further comprising the step of storing therein capturing media identification data and contamination testing results data.

6. The method of claim 5, and further including computer querying said testing results data and generating a notification signal whenever said contamination testing data exceeds a predetermined acceptability level.

7. The method of claim 1, wherein said particulate food is grain, and wherein said act of passing gas that was in contact with a material in the grain through a capturing media occurs after harvesting the grain.

8. The method of claim 7, wherein said act of passing grain gas that was in contact with said bulk particulate grain through a capturing media occurs before processing of said particulate grain into a final food product.

9. The method of claim 7, wherein said capturing media is marked with an identifier to identify at least the date and sample location captured by the media.

10. The method of claim 9, wherein said identifier includes a radio-frequency identification marker or bar code that is unique per capturing media.

11. The method of claim 9, further including a computer memory data storage system, and further comprising the step of storing therein capturing media identification data and contamination testing results data.

12. The method of claim 11, and further including computer querying said testing results data and generating a notification signal whenever said contamination testing data exceeds a predetermined acceptability level.

13. A method according to claim 1, wherein the gas from act 1(b) is gas taken while said particulate food is being moved.

14. A method according to claim 1, wherein the testing act 1(c) includes biological testing, and wherein said biological testing provides test results within a few hours and before said bulk quantity of food is mixed in with another bulk quantity of particulate food.

15. A method according to claim 5, 7, 8, 12 or 14, wherein the gas from act 1(b) is gas taken while said particulate food is being moved.

16. A method according to claim 1, 6, 7, 8 or 13, wherein the gas from act 1(b) is gas taken from space around said particulate food in a storage container, conveyor, augur, combine or dryer.

17. A method according to claim 1, 5, 7, 8, 12, 13 or 14, wherein the gas from act 1(b) is pumped through said capturing media, said media being changed out at time intervals, wherein said testing achieves a statistical confidence level of 90 to 99 percent confidence for testing of said bulk quantity of particulate food.

18. A method according to claim 1, 13 or 14, and further comprising the act of extracting or removing at least some of said material from said capturing media.

* * * * *

UNITED STATES PATENT AND TRADEMARK OFFICE
CERTIFICATE OF CORRECTION

PATENT NO. : 7,807,344 B2
APPLICATION NO. : 11/553163
DATED : October 5, 2010
INVENTOR(S) : Eric B. Dodd It is certified that error appears in the above-identified patent and that said Letters Patent is hereby corrected as shown below:

In claim 8, column 12, line 5, delete the word "grain".

In claim 15, column 12, line 31, change "claim" to --claims--.

In claim 16, column 12, line 34, change "claim" to --claims--.

In claim 17, column 12, line 38, change "claim" to --claims--.

Signed and Sealed this
Twenty-eighth Day of December, 2010

David J. Kappos
*Director of the United States Patent and Trademark Office*